United States Patent
Najafi et al.

(10) Patent No.: US 8,744,544 B2
(45) Date of Patent: Jun. 3, 2014

(54) SYSTEM HAVING WIRELESS IMPLANTABLE SENSOR

(75) Inventors: Nader Najafi, Ann Arbor, MI (US); Douglas Ray Sparks, Whitmore Lake, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 1026 days.

(21) Appl. No.: 12/253,540

(22) Filed: Oct. 17, 2008

(65) Prior Publication Data

US 2009/0105557 A1 Apr. 23, 2009

Related U.S. Application Data

(60) Provisional application No. 60/999,315, filed on Oct. 17, 2007.

(51) Int. Cl.
*A61B 5/05* (2006.01)
*A61B 5/02* (2006.01)

(52) U.S. Cl.
USPC .......................................... 600/345; 600/504

(58) Field of Classification Search
USPC .......................... 600/309, 345, 504, 505, 506
See application file for complete search history.

(56) References Cited

U.S. PATENT DOCUMENTS

| | | | |
|---|---|---|---|
| 5,425,775 A | 6/1995 | Kovacevic et al. | |
| 5,427,975 A * | 6/1995 | Sparks et al. | 438/52 |
| 5,531,121 A * | 7/1996 | Sparks et al. | 73/716 |
| 5,545,191 A * | 8/1996 | Mann et al. | 607/57 |
| 5,547,093 A * | 8/1996 | Sparks | 438/52 |
| 5,663,508 A | 9/1997 | Sparks | |
| 5,719,069 A * | 2/1998 | Sparks | 438/50 |
| 5,792,076 A | 8/1998 | Orsak et al. | |
| 6,034,296 A | 3/2000 | Elvin et al. | |
| 6,053,873 A * | 4/2000 | Govari et al. | 600/505 |
| 6,115,633 A * | 9/2000 | Lang et al. | 607/17 |
| 6,167,312 A | 12/2000 | Goedeke | |
| 6,277,078 B1 * | 8/2001 | Porat et al. | 600/486 |
| 6,309,350 B1 * | 10/2001 | VanTassel et al. | 600/300 |
| 6,312,380 B1 | 11/2001 | Hoek et al. | |
| 6,447,448 B1 | 9/2002 | Ishikawa et al. | |

(Continued)

OTHER PUBLICATIONS

H. Ayliffe and R. Rabbit, "An electric impedance based MEMS flow sensor for ionic solutions," Meas. Sci. Technol. 14, pp. 1321-1327, 2003.

(Continued)

*Primary Examiner* — Max Hindenburg
*Assistant Examiner* — Jonathan M Foreman
(74) *Attorney, Agent, or Firm* — Hartman Global IP Law; Gary M. Hartman; Domenica N. S. Hartman

(57) ABSTRACT

A system for monitoring a charge-based physiological parameter within an internal organ of a living body, and a sensor adapted to be implanted in the living body and an organ therein. The sensor includes sensing elements adapted to sense the charge-based physiological parameter within the organ, and the sensing elements include at least first and second sensing elements that are electrically conductive, aligned, spaced apart and exposed at the exterior of the sensor. The sensor further includes a device for passing an alternating current from the first to the second sensing elements through an ionic solution contacting the sensing elements. The sensor also includes a device for generating a signal corresponding to the impedance of the ionic solution based on the alternating current.

19 Claims, 9 Drawing Sheets

(56) References Cited

U.S. PATENT DOCUMENTS

| | | |
|---|---|---|
| 6,533,733 B1 | 3/2003 | Ericson et al. |
| 6,579,912 B2 | 6/2003 | Parfondry et al. |
| 6,645,143 B2 | 11/2003 | Van Tassel et al. |
| 6,647,778 B2 | 11/2003 | Sparks |
| 6,652,464 B2 | 11/2003 | Schwartz et al. |
| 6,656,135 B2 | 12/2003 | Zoghi et al. |
| 6,662,032 B1 | 12/2003 | Gavish et al. |
| 6,668,197 B1 | 12/2003 | Habib et al. |
| 6,682,480 B1 | 1/2004 | Habib et al. |
| 6,682,490 B2 | 1/2004 | Roy et al. |
| 6,692,446 B2 | 2/2004 | Hoek |
| 6,699,186 B1 | 3/2004 | Wolinsky et al. |
| 6,709,385 B2 | 3/2004 | Forsell |
| 6,709,390 B1 * | 3/2004 | Marie Pop .............. 600/368 |
| 6,712,778 B1 | 3/2004 | Jeffcoat et al. |
| 6,738,671 B2 | 5/2004 | Christopherson et al. |
| 6,746,404 B2 | 6/2004 | Schwartz |
| 6,764,446 B2 | 7/2004 | Wolinsky et al. |
| 6,890,303 B2 | 5/2005 | Fitz |
| 6,926,670 B2 | 8/2005 | Rich et al. |
| 6,968,734 B2 | 11/2005 | Tseng |
| 6,968,743 B2 * | 11/2005 | Rich et al. .............. 73/724 |
| 7,003,340 B2 | 2/2006 | Say et al. |
| 7,097,662 B2 | 8/2006 | Evans, III et al. |
| 7,174,199 B2 | 2/2007 | Berner et al. |
| 7,181,261 B2 | 2/2007 | Silver et al. |
| 7,263,882 B2 | 9/2007 | Sparks et al. |
| 7,922,667 B2 * | 4/2011 | Gianchandani et al. ...... 600/505 |
| 2002/0115920 A1 * | 8/2002 | Rich et al. ............ 600/345 |
| 2009/0105557 A1 * | 4/2009 | Najafi et al. ............ 600/301 |

OTHER PUBLICATIONS

S. Baumann et al., "The electrical conductivity of human cerebrospinal fluid at body temperature," IEEE Trans. Biomed. Engr. 44, No. 3, p. 220, Mar. 1997.

J. Latikka et al., "Conductivity of living intracranial tissues," Phys. Med. Biol. 46, pp. 1611-1616, 2001.

* cited by examiner

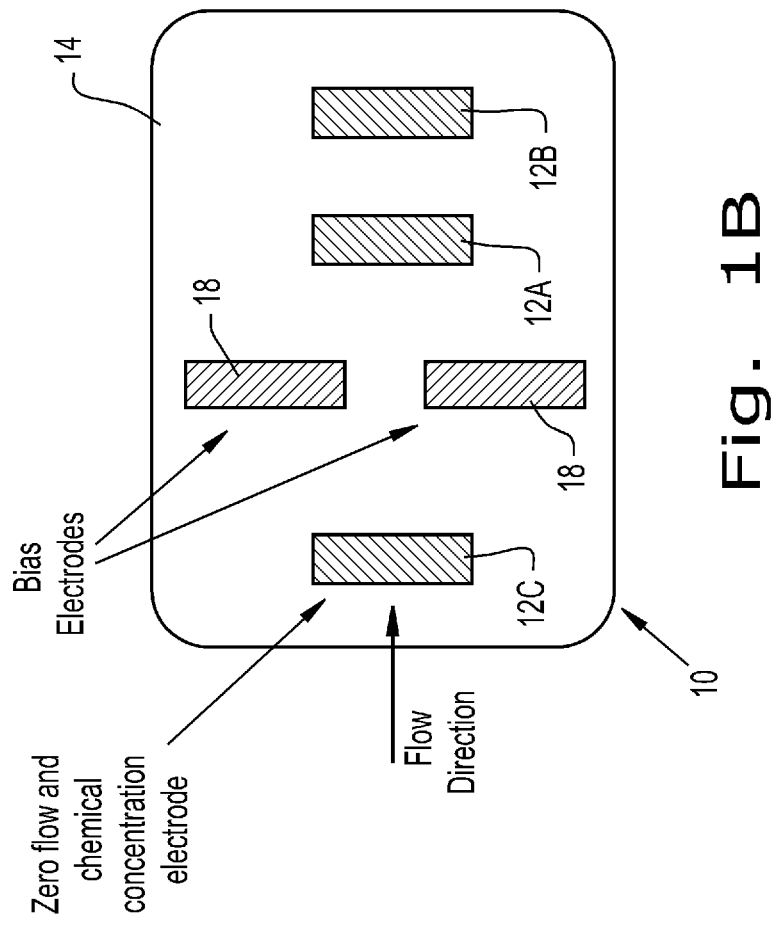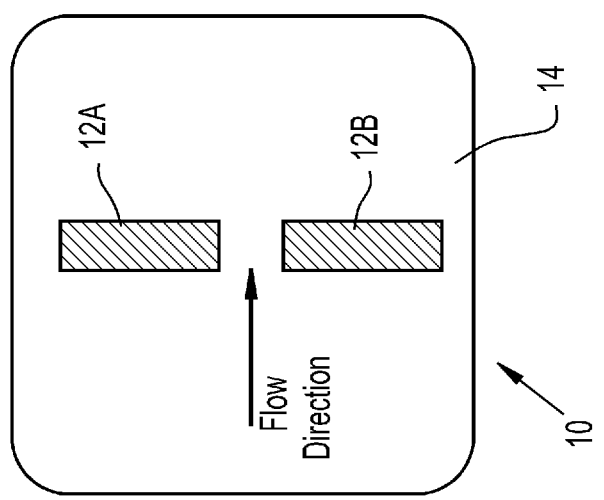

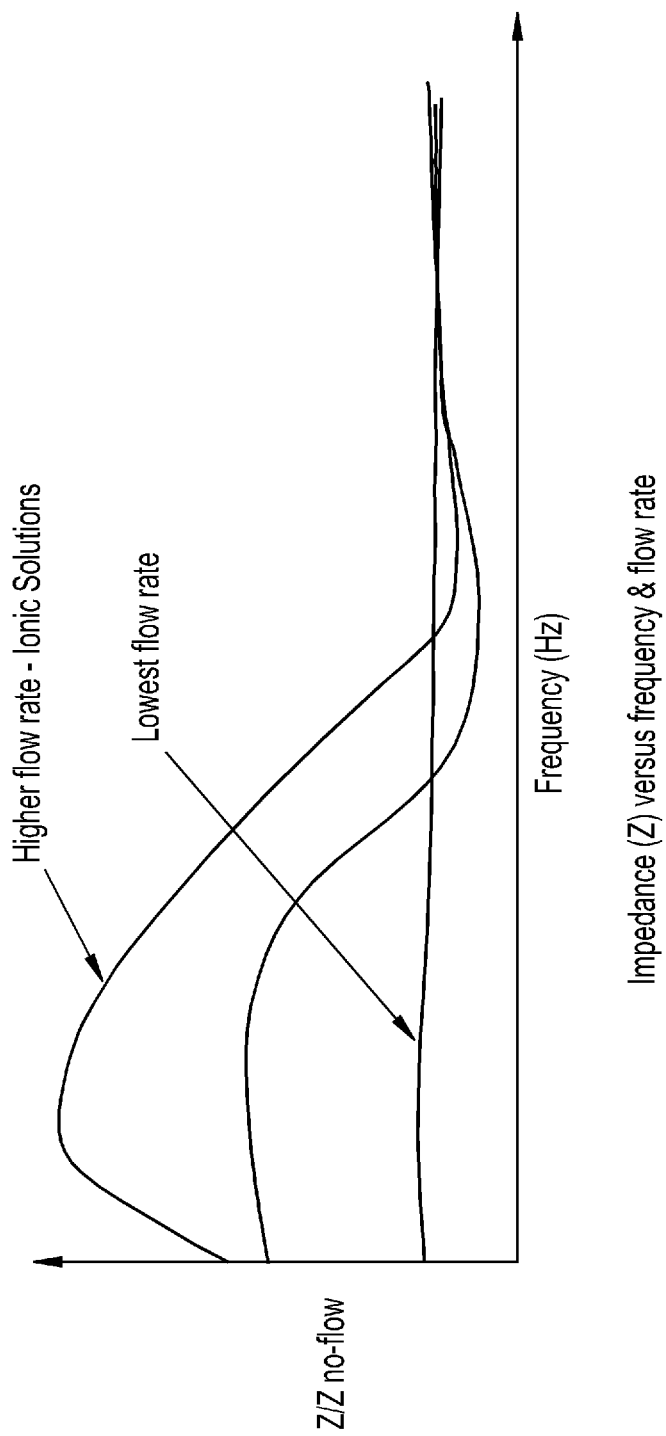

SYSTEM HAVING WIRELESS IMPLANTABLE SENSOR

CROSS REFERENCE TO RELATED APPLICATIONS

This application claims the benefit of U.S. Provisional Application No. 60/999,315, filed Oct. 17, 2007, the contents of which are incorporated herein by reference.

BACKGROUND OF THE INVENTION

The present invention generally relates to implantable sensing devices, and more particularly to an implantable sensing device equipped with electrodes to provide a flow and/or chemical sensing capability.

Wireless devices such as pressure sensors have been implanted and used to monitor heart, brain, bladder and ocular function. With this technology, capacitive pressure sensors are often used, by which changes in pressure cause a corresponding change in the capacitance of an implanted capacitor (tuning capacitor). The change in capacitance can be sensed, for example, by sensing a change in the resonant frequency of a tank or other circuit coupled to the implanted capacitor. The circuit can be implanted with the capacitor in the patient, and equipped with an antenna, such as a fixed coil, that receives a radio frequency (RF) signal transmitted from outside the patient to power the circuit, and also transmits the resonant frequency as an output of the circuit that can be sensed by a reader outside the patient. This approach has been applied to monitoring joint pressure, orthopedic conditions, intracranial, and cardiovascular pressures. Capacitive sensors can also be coupled with resistive strain gauges, accelerometers and optical fibers to monitor bone integrity. The necessity for implantable sensors to operate at very low currents and power levels, as well as the desire to minimize the overall size of the implant, complicates the implementation of flow rate sensors and chemical sensors that rely on such conventional sensing devices as hot-wire anemometers, piezoresistive sensors, and other flow meters with moving parts.

BRIEF DESCRIPTION OF THE INVENTION

The present invention provides an implantable sensor, sensing system, and sensing method suitable for sensing flow rates, chemical concentrations, conductivity, and pH of various fluids within or introduced into a human body by measuring charge-based parameters associated with ionic solutions in a manner that minimizes the power requirements of the sensor.

According to a first aspect of the invention, the sensor is part of a system for monitoring a charge-based physiological parameter within an internal organ of a living body, and the sensor is adapted to be implanted in the living body and an organ therein. The sensor includes sensing elements adapted to sense the charge-based physiological parameter within the organ, and the sensing elements include at least first and second sensing elements that are electrically conductive, aligned, spaced apart and exposed at the exterior of the sensor. The sensor further includes a device for passing an alternating current from the first to the second sensing elements through an ionic solution contacting the sensing elements. The sensor also includes a device for generating a signal corresponding to the impedance of the ionic solution based on the alternating current.

A significant advantage of this invention is the ability to measure flow rates, chemical concentrations, conductivities, pH, and other charge-based parameters of a wide variety of ionic fluids, including but not limited to blood, cerebral spinal fluid (CSF), lymph, interstitial fluids, urine, saline solution, ringers lactate, intravenous (IV) solutions, drugs, dialysates and other bodily fluids and fluids that may be injected, withdrawn or infused into a patient. CSF, blood and lymph contain ions such as Na+, Cl−, K+, Mg+, Ca++ and other ions used by the human body.

The sensor can be configured for placement in a fluid-carrying vessel, artery, vein, heart chamber, duct, spinal column, ventricle, shunt, ureter, urethra, tube, channel, implant or cannula, and can be integrated into shunts, smart shunts, valves, catheter, pressure sensors, and other sensor implants. For applications involving drugs and IVs, the sensor can be placed in the tubing going to and from the patient instead of being implanted directly into the patient.

Other objects and advantages of this invention will be better appreciated from the following detailed description.

BRIEF DESCRIPTION OF THE DRAWINGS

FIGS. 1A and 1B represent plan views of charge-based sense electrodes arranged on a surface of an implantable sensor for sensing flow, chemical concentration, or another charge-based parameter of an ionic fluid in accordance with embodiments of this invention.

FIG. 2 is a graph representing correlations between impedance, frequency, and flow rates as measured with charge-based sense electrodes of this invention.

DETAILED DESCRIPTION OF THE INVENTION

FIGS. 1A and 1B show examples of arrangements of sense electrodes 12 for sensing flow rates, chemical concentration, or another charge-based parameter of an ionic fluid in accordance with embodiments of this invention. In each of FIGS. 1A and 1B, a pair of sense electrodes 12 (designated as 12A and 12B) is shown on an outer surface 14 of a sensor 10. The electrodes 12A-B form a sensing element adapted to sense charged-based parameters of an ionic fluid using impedance measurements that are based on known principles, for example, as described in H. Ayliffe and R. Rabbit, "An electric impedance based MEMS flow sensor for ionic solutions," Meas. Sci. Technol. 14, pp. 1321-1327 (2003.). An electric current, typically about 0.1 milliamps or less alternating current at a frequency of about 100 Hz to about 100 kHz, is applied across the paired electrodes 12A-B. The electrodes 12A-B are sufficiently close together to insure that charged ions remain separated, enabling an impedance or charge measurement of the ionic fluid to take place with the electrodes 12A-B.

In FIG. 1A, the sensor 10 is oriented so that fluid flow is in a direction through a gap between the paired electrodes 12A-B. In the embodiment of FIG. 1B, the flow direction is aligned with the sense electrodes 12A-B, which include a third sense electrode 12C. Similar to the paired electrodes 12A-B, an AC current of up to about 0.1 milliamps at a frequency of about 100 Hz to about 100 kHz is applied across the electrodes 12A and 12C, enabling the electrodes 12A and 12C to sense charged-based parameters of an ionic fluid using impedance measurements. All three electrodes 12A-C are aligned, with the third electrode 12C separated from the electrodes 12A-B by a pair of biasing electrodes 18 held at a potential, for example, about 10 mV to about 10 VDC. The biasing electrodes 18 apply a biasing charge to ionize the ionic fluid being sensed, thereby achieving better separation of positive and negative ions within a transient ion cloud that travels across the sense electrodes 12A and 12B and the third electrode 12C located downstream and upstream, respectively, from the biasing electrodes 18. By comparing upstream measurements between the electrodes 12A and 12C to downstream measurements between the electrodes 12A and 12B, flow versus ion concentration measurements can be made and a zero-flowrate value can be estimated. Other configurations can be also be utilized, for example, other three-electrode schemes, and the invention encompasses such variations in electrode configurations.

Figure 3:
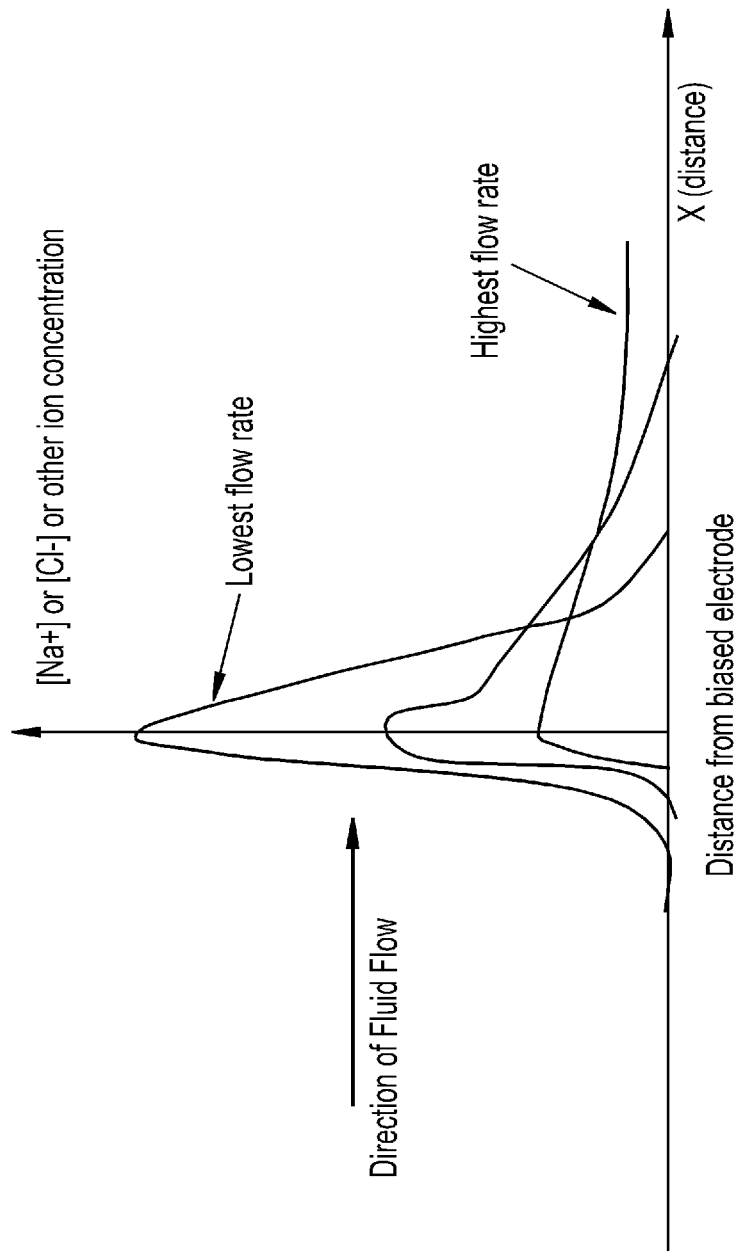
FIG. 3 is a graph representing correlations between ion concentrations, flow rates and distance from charge-based sense electrodes of this invention.

FIG. 2 shows how the impedance ratio of flow to no flow as a function of frequency can be used with the electrode arrangements of FIGS. 1A and 1B to measure flow rates. The phase as a function of frequency can also be used to monitor flow rate. FIG. 3 illustrates that the charge ion concentration may vary over distance from the bias electrodes 18, similar to how thermal flow sensing elements measure flow rate using a hot wire element.

By using photolithography methods, patterned metal electrodes 12 and 18 can be formed to define small gaps therebetween, for example, less than one hundred micrometers between the paired electrodes 12A-B, preferably a few micrometers up to tens of micrometers, which is sufficient to insure that a significant percentage of separated positive and negative ions will be present at and between the electrodes 12A-B. The electrodes 12 and 18 should be resistant to corrosion in the ionic solution being assessed. For this reason, platinum, palladium, silver, titanium, and iridium alloys and silver oxide are believed to be well suited as materials for the electrodes 12 and 18. For AC and charge measurements, the electrodes 12 and 18 can be passivated with a thin dielectric corrosion resistant layer. The electrodes 12, which may be in any suitable form, including two-dimensional structures (for example, flat pads or contacts) and three-dimensional structures (for example, probes, etc.) that protrude from the sensor surface 14, and are connected to electronic components as well as an inductor coil that form part of the sensor 10, as discussed below.

Figure 4A:
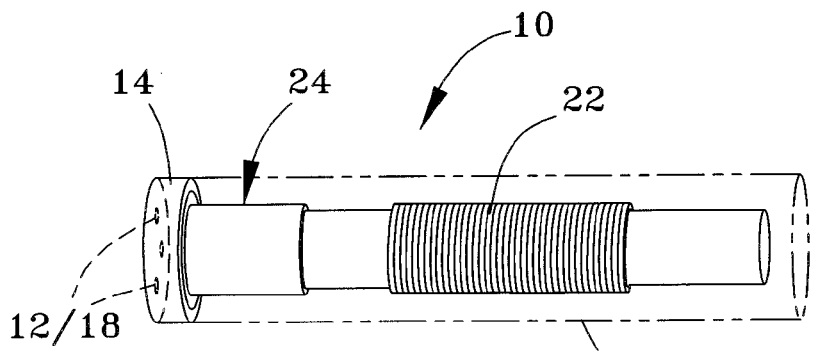
FIGS. 4A through 4G represent various embodiments for implantable sensors that can be equipped with charge-based sense electrodes of this invention.

The sensor 10 incorporating the sensing element formed by the electrodes 12 and 18 of FIGS. 1A and 1B can have a wide variety of configurations, including cylindrical and disk-shaped exteriors. FIGS. 4A-4G and 5 represent some of the possible configurations, and in these figures consistent reference numbers are used to identify functionally similar structures. In FIG. 4A, the sensor 10 is represented as a sealed cylindrical-shaped capsule. A hermetic housing 20 encloses a core and coil assembly 22 and electronics 24 (for example, printed circuit boards (PCBs) and/or application-specific integrated circuits (ASICs)), with only the electrodes 12 and 18 (of which only 12A and 12B are shown) exposed at the external surface 14 of the housing 20. The electrodes 12A-B are shown as located at the end of the cylindrical-shaped housing, though it is foreseeable that the electrodes 12 and 18 could be located elsewhere, for example, along the sides of the housing 20. The sense electrodes 12 and possibly some of the electronics 24 may be mounted on a substrate, connected together using various methods known in the art, for example, wirebonding, flexible connectors, etc., or potted together using a biocompatible epoxy or any other suitable potting material.

The surface 14 carrying the sense electrodes 12 can be either rigid or flexible substrate material, or a combination (for example, a rigid-flex substrate, where part of the substrate is rigid and another part is flexible). In the case of flexible substrates, various polymers, Parylene, silicone, or other biocompatible flexible material may be used. In the case of rigid substrates, glass, silicon, ceramics, carbides, alloys, metals, hard polymers, Teflon, are some examples, although other types of materials can also be used. In the case of rigid-flex substrates, the rigid and flexible parts may be made from dissimilar material. The electrodes 12 themselves, especially three-dimensional electrodes 12, can also either be rigid, flexible, or a combination. For example the electrodes 12 can be formed by a flexible three-dimensional element made from polymers, Parylene, silicone, etc., which is partially or fully metallized. The electrodes 12 may also have a flexible tip portion connected to a rigid portion connected to the substrate surface 14, or alternatively may have a rigid tip portion connected to the substrate surface 14 via a flexible portion. The rigid and flexible portions may be made from similar or dissimilar material.

Figure 4B:
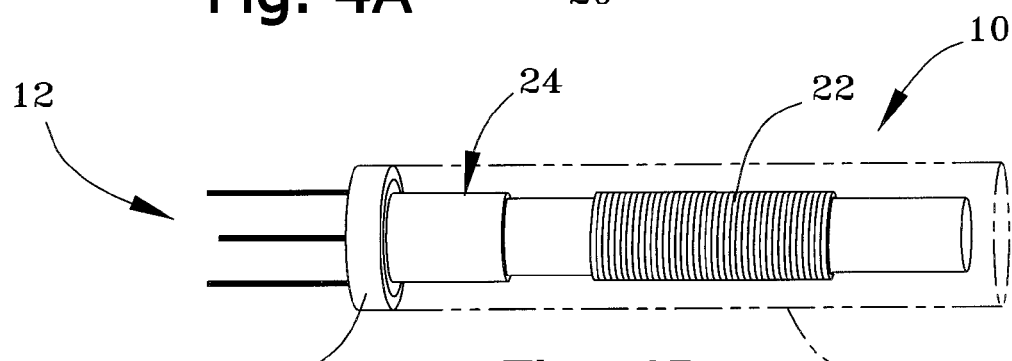
Figure 4C:
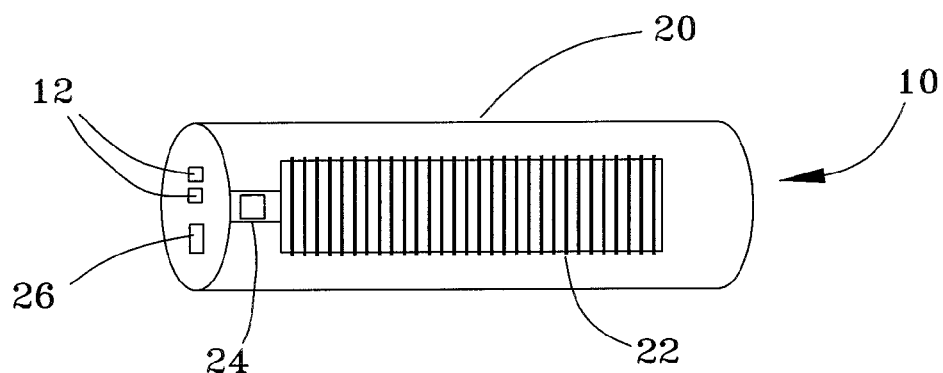

FIGS. 4B and 4C are similar to FIG. 4A, but show the electrodes 12 and 18 protruding from the housing 20 (FIG. 4B) and the inclusion of a second element 26 (FIG. 4C), which may be another sensing element adapted to sense a different parameter or an actuating element adapted to physically induce, stimulate, or respond to conditions within the ionic fluid being evaluated by the sensor 10. As nonlimiting examples, the sensor 10 can further incorporate various other miniature sensing elements adapted to detect and/or monitor various physiological parameters of a patient, such as pressure, strain, temperature, and/or velocity sensors, and/or measure specific chemistries such as gas content (for example, O2 and CO2) and glucose levels, or incorporate various miniature actuators, including but not limited to thermal generators, voltage sources, current sources, probes, electrodes, drug delivery pumps, valves, meters, microtools for localized surgical procedures, radiation emitting sources, defibrillators, muscle stimulators, and pacing stimulators. Various specific examples of these types of miniature sensors and actuators are known to those skilled in the art, and any one or more of these can be utilized in the sensor 10 of the present invention if capable of sufficiently small size to permit placement of the sensor 10 within a catheter for delivery and implantation, or otherwise permit surgically implanted.

A particular example is to incorporate a pressure sensor into the sensor 10 for patients with traumatic brain injury to monitor brain pressure to allow for tailoring of the sensor operation. By measuring different physiologic parameters, the sensor 10 can use the measured physiologic parameter(s) to control, adjust or manipulate and the stimulating function (for example, patter, frequency, location, amplitude, etc.). This approach allows dynamic and smart stimulation and allows the implementation of a closed-loop system. For example, if the implanted sensor 10 is adapted to sense flow, the sensor 10 can operate with other implanted or non-implanted devices (such as sensors, actuators, valves, etc.) as part of a closed loop control system which can stimulate, monitor, measure one or more physiological parameter, and perform additional actions all based on feedback from one or more of the units in the system.

Figure 4D:
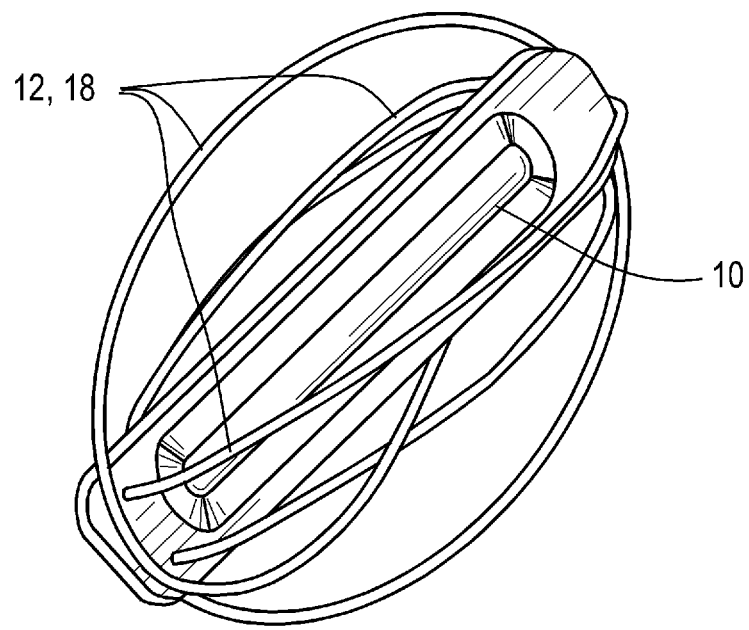
Figure 4E:
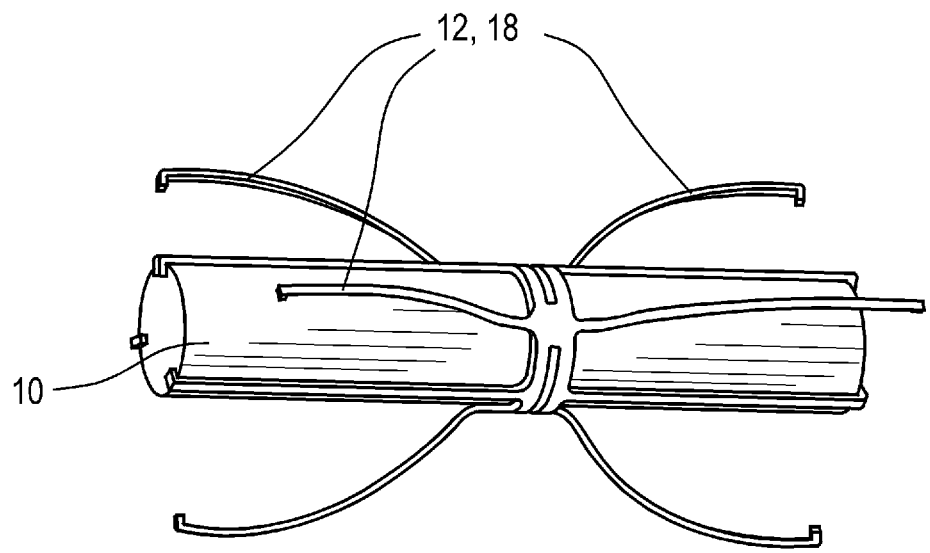

FIGS. 4D and 4E depict further embodiments of cylindrical-shaped sensors 10, in which the electrodes 12 and/or 18 protrude from the housing 20 to define anchoring features. In FIG. 4D, the electrodes 12/18 are in the form of wire loops that are connected to and arcuately extend between the opposing ends of the housing 20. In FIG. 4E, the electrodes 12/18 are in the form of wire arms that are attached at an intermediate region of the housing 20 and arcuately extend toward the opposing ends of the housing 20. In each case, the electrodes 12/18 permit the sensor 10 to be placed and anchored within a tubular-shaped passage, such as an artery.

Figure 4G:
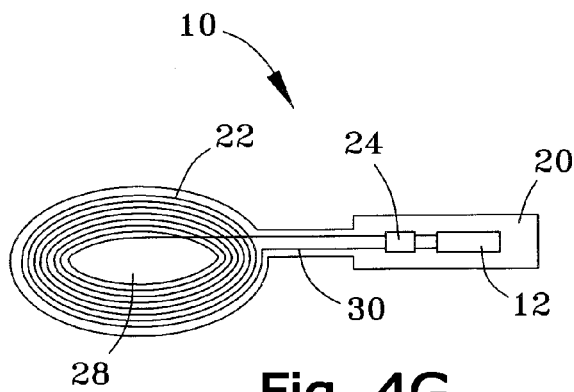
Figure 4F:
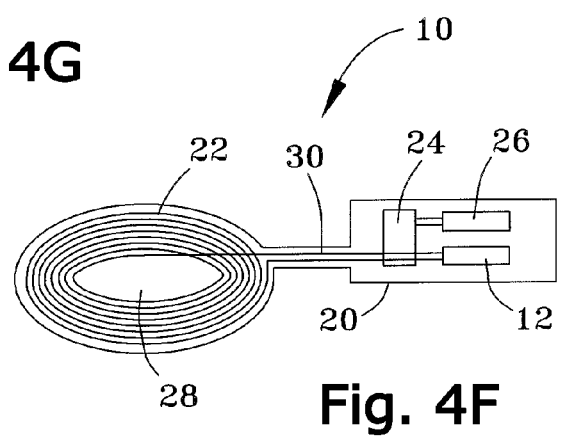
Figure 10:
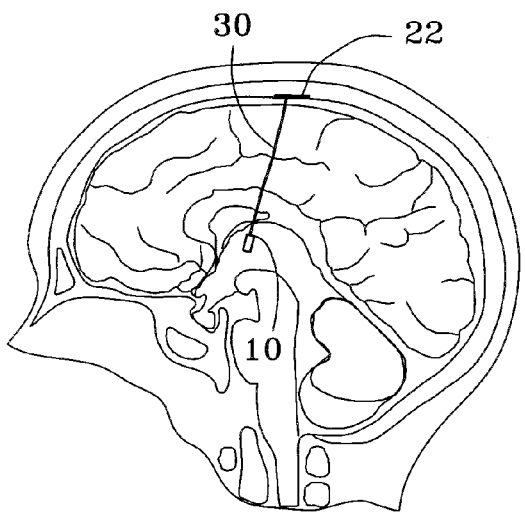
FIGS. 10 and 11 represent techniques for intracranial placement of implantable sensors of this invention for sensing flow, chemical concentration, or another charge-based parameter of cerebral spinal fluid in accordance with embodiments of this invention.
Figure 11:
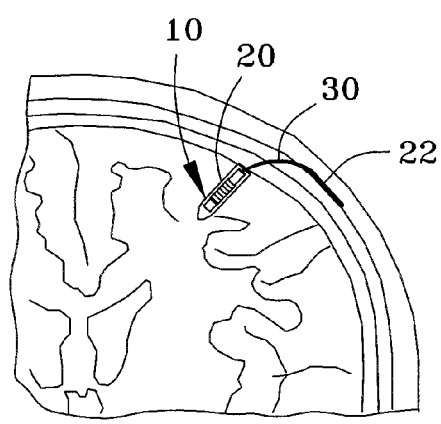

FIGS. 4F and 4G represent sensors 10 configured for use in intracranial applications to monitor the cerebral spinal fluid of a patient. For this purpose, the housing 20 containing the electrodes 12, electronics 24, etc., is adapted for deep implantation within the brain, whereas the antenna 22 is fabricated on a flexible or rigid film 28 that can be located remove from the sensor 10, as represented in FIG. 10. A cable 30 interconnects the implantable housing 20 with the antenna 22. FIG. 4F differs from FIG. 4G by the inclusion of a second element 26, similar to FIG. 4C. FIG. 11 represents a similar implantation, but with a cylindrical antenna 22 similar to the core and coil assembly 22 of FIGS. 4A through 4E. The antenna 22 (and any packaging thereof) can be attached to the skull and placed under the scalp, or attached under the skull above the dura mater such that it does not pierce the dura, or placed outside the body (for example, attached on top of the scalp). An advantage of the sensor configurations of FIGS. 4F, 4G, 10 and 11 is the ability for a very small footprint for the implanted portion of the sensor 10 within the brain (or another location), while bulkier portions of the sensor 10 are placed at a separate and possibly more favorable location.

Figure 5:
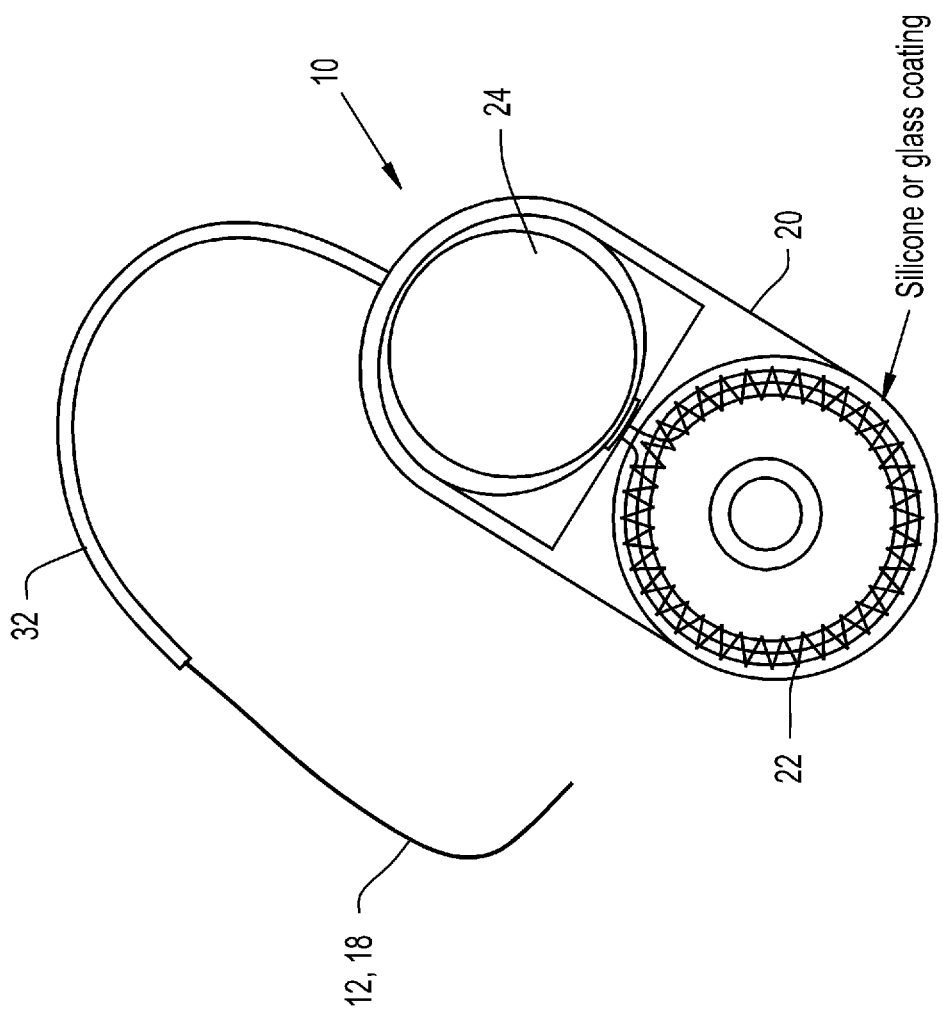
FIG. 5 represents an embodiment of a non-implantable sensor having an implantable lead that can be equipped with charge-based sense electrodes of this invention.

FIG. 5 shows yet another alternative for implementing the electrodes 12 and 18 of FIGS. 1A and 1B. In FIG. 5, the electrodes 12 and 18 are disposed outside the sensor housing 20 at the end of a cable 32, and therefore somewhat remote from the antenna 22 and electronics 24 sealed within the housing 20.

The implantable sensor 10 and its components may be physically realized with a combination of any of several technologies, including those using microfabrication technology such as microelectromechanical systems (MEMS). The housing 20 can be made from a variety of materials, such as glass, ceramics, polymers, silicone, Parylene, etc. The hermetic sensor housing 20 may also be formed from anodically bonded layers of glass and silicon (doped or undoped). Alternatively, the internal components of the sensor 10 may be potted together using known biocompatible materials to effectively form the exterior of the housing 20. In some cases, it may be desirable to apply additional materials (organic, metal, or any biocompatible material) to the exterior of the housing 20 to protect certain regions of the sensor 10. For example, a coating may be applied to all but the electrodes 12 and 18, or the electrodes 12 and 18 may be coated with a material that differs from the material applied to the remainder of the sensor housing 20. Examples of suitable coating materials include polymers, Parylene, silicone, hydrogels, titanium, nitrides, oxides, carbides, silicides, etc.

The sensors 10 represented in FIGS. 4A-4G and 5 can be integrated into other systems, such as shunts, valves, pumps, tubing, defibrillators, drug pumps, pacemakers, neural stimulators, deep brain stimulators, and other implantable devices.

Figure 6:
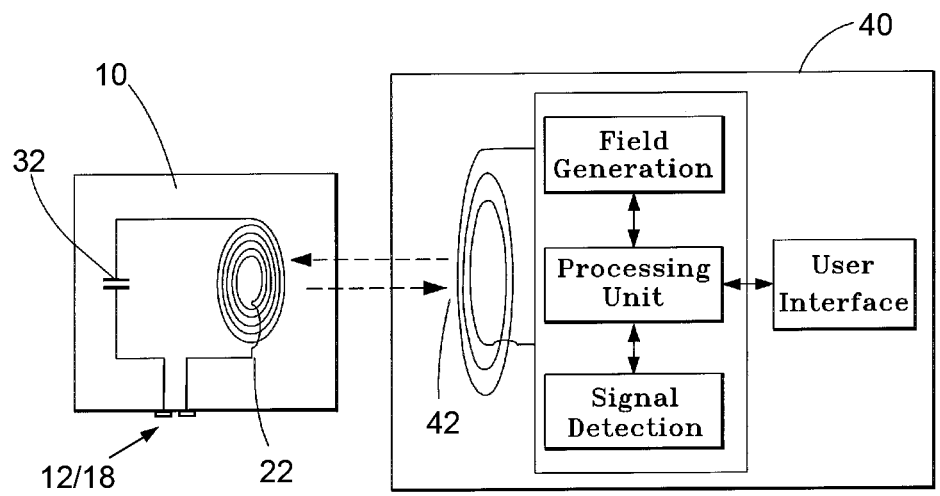
FIGS. 6 and 7 are block diagrams of wireless pressure monitoring systems that utilize resonant and passive sensing schemes, respectively, which can be utilized by monitoring systems of this invention.
Figure 7:
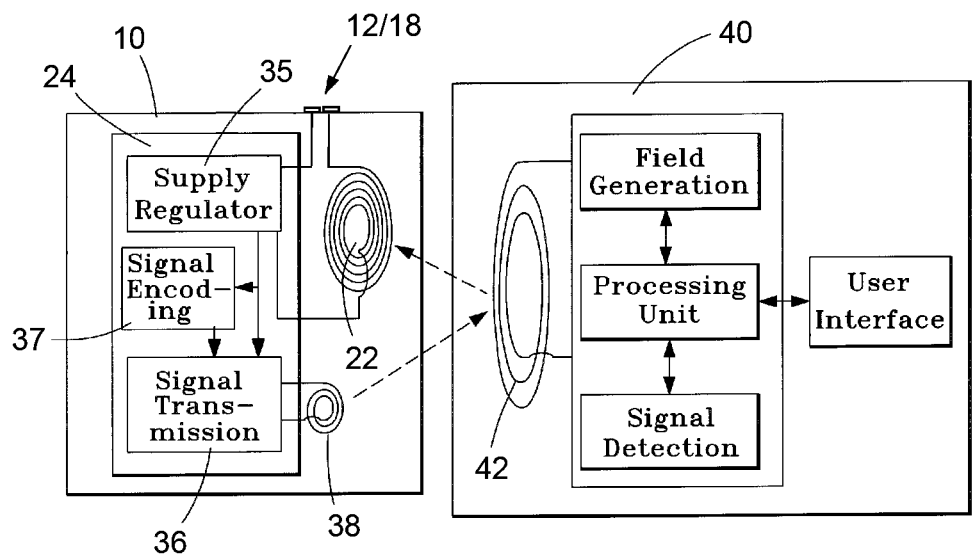

FIGS. 6 and 7 represent two types of wireless telemetry schemes that can be utilized with the invention to noninvasively monitor the sensor 10 and evaluate the health of the patient as well as the operation of the sensor 10. These schemes are disclosed in commonly-assigned U.S. Pat. Nos. 6,926,670 and 6,968,734 to Rich et al., whose contents are incorporated herein by reference. In FIG. 6, the sensor 10 is shown as operating in combination with a non-implanted external reader unit 40, between which a wireless telemetry link is established using a resonant scheme. The sensor 10 contains the sense electrodes 12 (and optionally the biasing electrodes 18), the antenna 22, and a capacitor 32. The antenna 22 serves as an inductor coil, and together the antenna 22 and capacitor 32 form an LC (inductor-capacitor) tank resonator circuit that has a specific resonant frequency, expressed as $1/(LC)^{1/2}$, which can be detected from the impedance of the circuit. Notably, the impedance across the sense electrodes 12 influences the impedance of the tank circuit. At the resonant frequency, changes in the impedance sensed with the electrodes 12 present measurable changes in magnetically-coupled impedance load to an external coil 42 associated with the reader unit 40. Based on the antenna 22 and capacitor 32 being fixed and therefore having fixed inductance and capacitance values, the reader unit 40 is able to determine the impedance sensed by the electrodes 12 by monitoring the resonant frequency of the circuit. The reader unit 40 is then able to determine the charged-based parameter being sensed by the electrodes 12, for example, flow rate, by monitoring the frequency at which the impedance of the antenna 22 or ionic charge changes.

FIG. 7 shows the sensor 10 modified to operate in combination with a modified reader unit 40. A wireless telemetry link is established between the sensor 10 and reader unit 40 using a passive, magnetically-coupled scheme, in which onboard circuitry of the sensor 10 receives power from the reader unit 40. In the absence of the reader unit 40, the sensor 10 lays passive and without any internal means to power itself. When a reading is desired, the reader unit 40 must be brought within range of the sensor 10.

In FIG. 7, the sensor 10 again contains the sense electrodes 12 (and optionally the biasing electrodes 18) and the antenna 22, which serves as an inductor coil, and the reader unit 40 again has a coil 42 by which an alternating electromagnetic field is transmitted to the antenna 22 of the sensor 10 to induce a voltage in the sensor 10. When sufficient voltage has been induced in the sensor 10, a supply regulator (rectification) circuitry 35 converts the alternating voltage on the antenna 22 into a direct voltage that can be used by the electronics 24 as a power supply for signal conversion and communication. At this point the sensor 10 can be considered alert and ready for commands from the reader unit 40. The sensor 10 may employ the antenna 22 as an antenna for both reception and transmission, or it may utilize the antenna 22 solely for receiving power from the reader unit 40 and employ a second coil 38 for transmitting signals to the reader unit 40. Signal transmission circuitry 36 receives an encoded signal generated by signal conditioning circuitry 37 derived from the output of the electrodes 12, and then generates an alternating electromagnetic field that is propagated to the reader unit 40 with the antenna 22 or coil 38. The reader unit 40 may interface to a user interface, which may include a display, computer, or other data logging devices.

A large number of possible geometries and structures are known and available for the antennas/coils 22, 38 and 42 of FIGS. 6 and 7. The coil conductors may be wound around a ferrite core to enhance magnetic properties, deposited on a flexible substrate, or formed into a cylindrical-shaped cover. The coil conductors are preferably made at least in part with a metal of high conductivity, such as copper, platinum, silver, gold, etc. The coil conductors may alternately be fabricated on implantable substrates. Methods of fabrication of coils on substrates include but not limited to one or more or any combination of the following techniques: sputtering, electroplating, lift-off, screen printing, and other suitable methods known to those skilled in the art.

As previously noted, the supply regulator (rectification) circuitry 35 converts the alternating voltage on the antenna 22 into a direct voltage that can be used by the electronics 24 as a power supply for signal conversion and communication. Efficient realization of such a circuit can employ standard electronic techniques and may include full-bridge or half-bridge diode rectifiers. The rectification circuitry 35 may include a capacitor for transient energy storage to reduce the noise ripple on the output supply voltage. The rectification circuitry 35 may be implemented on the same integrated circuit die with other components of the electronics 24. Many different circuits for the signal transmission circuitry 36 and signal conditioning circuitry 37 are also known to those skilled in the art. Impedance- and capacitance-to-frequency conversion, sigma delta, and other analog-to-digital conversion techniques are all possible conditioning circuits that may be used.

In a preferred embodiment of the invention, the readout unit 40 receives data from the sensor 10 using the 13.56 MHz ISM band. Two modes of operation can be employed: (1) a data-logging measurement mode with optional data rates of, for example, 1 Hz and below, and (2) a real-time dynamic measurement mode with data rates of, for example, 100 to 500 Hz, for compliance and impulse tests. The readout unit 40 is represented in FIGS. 6 and 7 as comprising analog RF front end electronics providing processing and user interface capabilities. A graphical user interface program can be used to control information (e.g., ICP monitor) and created in, for example, the LabVIEW and C visual programming languages.

The external readout unit 40 can be adapted to perform one or more of the following: remote monitoring of patients, including but not limited to home monitoring; monitoring of patients with telephone-based (or similar method) data and information delivery; monitoring of patients with wireless telephone-based (or similar method) data and information delivery; monitoring of patients with web-based (or similar method) data and information delivery; closed-loop drug delivery to treat diseases; warning systems for critical worsening of diseases and related conditions; portable or ambulatory monitoring or diagnostic systems; battery-operation capability; data storage; reporting global positioning coordinates for emergency applications; communication with other medical devices including but not limited to pacemakers, defibrillator, implantable cardioverter defibrillator, implantable drug delivery systems, non-implantable drug delivery systems, and wireless medical management systems.

The sensor 10 is shown in FIG. 7 without a battery, and therefore its operation does not require occasional replacement or charging of a battery. Instead, the energy required to perform the sensing operation is entirely derived from the reader unit 40. However, the sensor 10 could be modified to use an additional capacitor, battery, rechargeable battery, or other power storage device to power the sensor 10 when the reader unit 40 is not sufficiently close to induce a voltage in the sensor 10. Such an active scheme option is particularly useful for (but not limited to) situations in which long-term data acquisition without continuous use of the readout unit is desirable. With an on-board power source, data may be stored in the sensor 10 and downloaded intermittently using the readout unit 40 as required.

As those skilled in magnetic telemetry are aware, a number of modulation schemes are available for transmitting data via magnetic coupling. Particularly suitable schemes include but are not limited to amplitude modulation, frequency modulation, frequency shift keying, phase shift keying, and also spread spectrum techniques. A preferred modulation scheme may be determined by the specifications of an individual application, and is not intended to be limited under this invention.

In addition to the many available modulation techniques, there are many technologies developed that allow the sensor 10 to communicate the charge-based parameter signal to the reader unit 40. It is understood that the reader unit 40 may transmit either a continuous level of RF power to supply the sensor 10 with needed energy, or the reader unit 40 may pulse the power allowing temporary storage in a battery or capacitor device. Similarly, the sensor 10 of FIG. 7 may signal back to the reader unit 40 at any interval in time, delayed or instantaneous, during reader RF transmission or alternately in the absence of reader transmission. If periodic functioning of the sensor 10 is employed, a charging phase may be employed during which a storage device (such as a capacitor, rechargeable battery, etc.) within the sensor 10 is charged, while flow measurements are made during another phase of operation that may be entirely separate or overlap the charging phase.

The sensor 10 and its companion reader unit 40 permit a physician, caregiver or patient to monitor the sensor 10 at any time, and can be employed for home care and monitoring as well as in a hospital or physician's office. The sensor 10 and reader unit 40 may be implemented as a remote monitoring system, including but not limited to home monitoring, which may include telephone-based, wireless communication-based, web-based, etc., delivery of information received from the sensor 10 by the reader unit 40 and then presented to a physician or caregiver. Information such as the patient's name, current weight, prior weight (for example, prior to surgery), body temperature, blood pressure and posture can all be entered into the reader unit 40 before a measurement is taken to assist in obtaining an accurate reading and arriving at appropriate decisions about the integrity of the sensor 10. The sensor 10 or its reader unit 40 can also perform algorithms to account for pressure or strain changes and its affect on flow rate due to the position of the patient, weight gain, body temperature.

Figure 8:
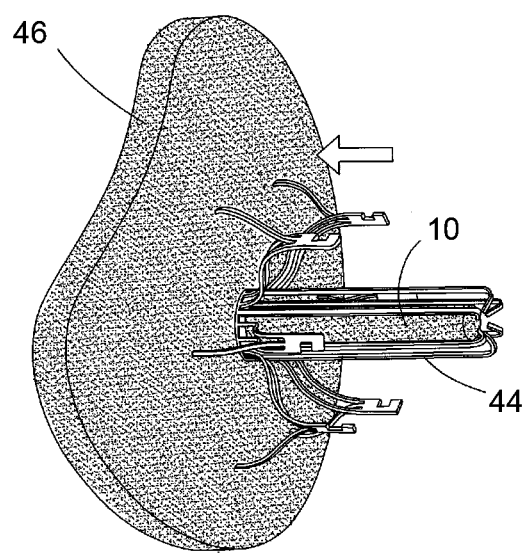
FIGS. 8 and 9 represent use of the anchor to place an implantable sensor of this invention in a wall for sensing flow, chemical concentration, or another charge-based parameter of an ionic fluid in accordance with embodiments of this invention.
Figure 9:
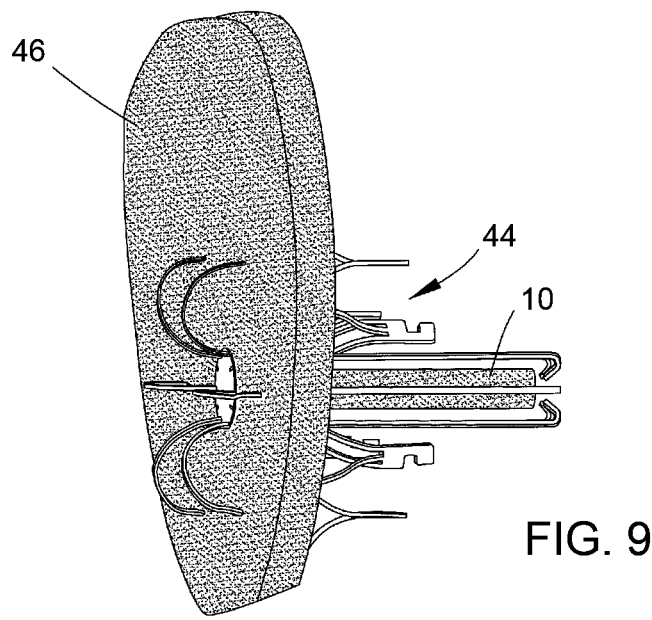

The sensor 10 can be implanted using a surgical procedure or a minimally-invasive outpatient technique. The insertion and placement of the sensor 10 into the brain (and various other locations) can be a relatively simple procedure and done by a trained technician rather than a highly specialized surgeon. This aspect of the invention is an important advantage over existing flow sensing devices. If configured similar to that shown in FIGS. 4A through 4E, the sensor 10 can be implanted using catheter insertion method. For example, the sensors 10 shown in FIGS. 4D and 4E can be attached or lodged in a duct or other tubular-shaped passage (e.g., an artery or IV tube) for measurement of a fluid flowing through the duct. Alternatively, FIGS. 8 and 9 depict a method by which the sensor 10 can be delivered surgically or via a catheter and anchored within an opening in a wall 46 so that only the electrodes 12 protrude into a flow path within a cavity defined by the wall 46. In the embodiment of FIGS. 8 and 9, the sensor 10 is placed within an anchor 44 disclosed in commonly-assigned U.S. patent application Ser. No. 11/684,910, whose contents are incorporated herein by reference.

Alternatively, anchoring provisions may be incorporated directly into the housing 20, or incorporated directly into the housing 20 by additional assembly steps (for example, FIGS. 4D and 4E). For example, various anchoring features and fasteners known in the art could be used, including those adapted to attach to the skull or scalp using wires, screws (helical or otherwise), bolts, mesh, stents, springs, stitches, expandable tines, etc. Suitable anchoring mechanisms can also form part of another device with which the sensor 10 is implanted. For example, in patients with hydrocephalus, the anchoring mechanism can be part of the shunt used for draining the excess fluid. Suitable materials for anchors used with the sensor 10 include, but not limited to, Nitinol, Teflon, Parylene, polymers and metals.

In view of the foregoing, it should be apparent that blood flow measurement is a notable medical application of the sensor 10, as well as its expansion to cardiac output measurement. Another important medical application is hydrocephalus shunts that can measure CSF flow discharge, sense whether the shunt is clogged, provide advance warning for changing the shunt, detect false emergencies, and timely detect actual emergencies. In all such applications, multiple sensors 10 may be used, either in close proximity, or in separate locations. The multiple sensors 10 may each be a completely separate unit and not share any common elements, or share a common coil or other sensor component. In some cases, the sensor 10 may include or be used with multiple stimulating electrodes on either the same or multiple different substrates.

The sensor 10 can be implanted in a variety of internal organs, glands, ducts, and vessels, including but not limited to the heart, brain, kidneys, lungs, bladder, ureter, urethra, spinal cord, arteries, veins, lymph ducts, reproductive systems, and abdomen. The sensor 10 and its systems can be used in the treatment of many different disease, including but not limited to cardiovascular disease, depression, Parkinson's disease, multiple sclerosis, amyotrophic lateral sclerosis (ALS, often referred to as "Lou Gehrig's disease") Alzheimer's, borderline personality, compulsive disorders, addictions, stroke, brain trauma, brain injury, inflammation in the brain, tumors, hydrocephalus, cerebral palsy, essential tremor, coma, mental retardation, dystonia, and tremor due to multiple sclerosis. The sensor 10 and its system can significantly improve the tailored treatment of many severe diseases as a result of offering an easy to use and a relatively low-cost option for performing non-invasive, realtime, detailed and chronic monitoring/stimulation at home, in the doctor's office, or in the hospital.

While the invention has been described in terms of specific embodiments, it is apparent that other forms could be adopted by one skilled in the art. For example, the physical configuration of the sensor 10 could differ from that shown, and materials and processes other than those noted could be used. Therefore, the scope of the invention is to be limited only by the following claims.

The invention claimed is:

1. A system for monitoring a charge-based physiological parameter of an ionic fluid within an internal organ of a living body, the system comprising at least one sensor adapted to be implanted in the living body and an organ therein, the sensor comprising:

a surface defining an exterior of the sensor relative to which the ionic fluid flows in a flow direction;

sensing elements adapted to sense the charge-based physiological parameter of the ionic fluid within the organ, the sensing elements comprising at least first and second sensing elements that are electrically conductive, aligned and spaced apart in the flow direction, and exposed at the exterior of the sensor so as to be contacted by the ionic fluid;

means for applying an alternating current in the flow direction, between the first and second sensing elements, and through the ionic fluid contacting the first and second sensing elements;

means for applying a biasing charge in a direction transverse to the flow direction to ionize the ionic fluid in a direction from the first and second sensing elements opposite the flow direction; and means for generating a signal corresponding to the impedance of the ionic fluid based on the alternating current.

2. The system according to claim 1, wherein the charge-based physiological parameter sensed by the first and second sensing elements is chosen from the group consisting of flow rates, chemical concentrations, conductivity, and pH of the ionic fluid.

3. The system according to claim 1, wherein the ionic fluid is chosen from the group consisting of blood, cerebral spinal fluid, lymph, interstitial fluids, urine, saline solution, ringers lactate, intravenous solutions, drugs and dialysates.

4. The system according to claim 1, further comprising a readout device that is not adapted to be implanted in the living body, the readout device comprising means for establishing a wireless telemetry link with the sensor to obtain a reading of the charge-based physiological parameter.

5. The system according to claim 1, wherein the first and second sensing elements are pads that do not protrude from the surface.

6. The system according to claim 1, wherein the first and second sensing elements protrude from the surface.

7. The system according to claim 1, wherein the first and second sensing elements are disposed at a distal end of a wire that protrudes from the surface.

8. The system according to claim 1, wherein the means for applying the biasing charge to ionize the ionic fluid comprises a pair of biasing electrodes aligned and spaced apart in a direction transverse to the flow direction and transverse to the alignment of the first and second sensing elements.

9. The system according to claim 8, wherein the sensor further comprises a third sensing element aligned with the first and second sensing elements in the flow direction and spaced apart from the first and second sensing elements in the flow direction, and the pair of biasing electrodes are between the first and second sensing elements and the third sensing element.

10. The system according to claim 9, wherein the sensor further comprises means for applying an alternating current through the ionic fluid from the third sensing element to one of the first and second sensing elements in the flow direction.

11. The system according to claim 1, further comprising means for anchoring the sensor within a tubular-shaped passage.

12. The system according to claim 11, wherein the anchoring means comprises the first and second sensing elements, which protrude from the surface of the sensor.

13. The system according to claim 1, further comprising means for anchoring the sensor to a wall.

14. The system according to claim 1, wherein the sensor further comprises an additional sensing element adapted to sense an additional physiological parameter chosen from the group consisting of pressure, strain, temperature, and velocity.

15. The system according to claim 1, wherein the sensor further comprises an actuator.

16. A method of using the system of claim 1 to monitor the charge-based physiological parameter of the ionic fluid, the method comprising:
   implanting the sensor within an internal organ of a living body so that the ionic fluid flows in the flow direction and the first and second sensing elements are aligned and spaced apart in the flow direction and contacted by the ionic fluid;
   applying the alternating current from the first to the second sensing elements through the ionic fluid contacting the first and second sensing elements; and
   generating the signal corresponding to the impedance of the ionic fluid based on the alternating current.

17. The method according to claim 16, further comprising applying a biasing charge through the ionic fluid and in a direction transverse to the flow direction to ionize the ionic fluid in a direction from the first and second sensing elements opposite the flow direction.

18. The method according to claim 17, wherein the biasing charge is applied with a pair of biasing electrodes aligned and spaced apart in a direction transverse to the flow direction and transverse to the alignment of the first and second sensing elements.

19. The method according to claim 18, wherein the sensor further comprises a third sensing element aligned with the first and second sensing elements in the flow direction and spaced apart from the first and second sensing elements in the flow direction, the pair of biasing electrodes are between the third sensing element and the first and second sensing elements, and the method further comprises applying an alternating current through the ionic fluid and from the third sensing element to one of the first and second sensing elements in the flow direction.

* * * * *